United States Patent
Champagne

(10) Patent No.: US 11,826,442 B2
(45) Date of Patent: Nov. 28, 2023

(54) COSMETIC CLEANSING FORMULATION

(71) Applicant: COATEX, Genay (FR)

(72) Inventor: Clementine Champagne, Caluire-et-Cuire (FR)

(73) Assignee: COATEX, Genay (FR)

( * ) Notice: Subject to any disclaimer, the term of this patent is extended or adjusted under 35 U.S.C. 154(b) by 112 days.

(21) Appl. No.: 17/255,205

(22) PCT Filed: Jul. 1, 2019

(86) PCT No.: PCT/FR2019/000108
§ 371 (c)(1),
(2) Date: Dec. 22, 2020

(87) PCT Pub. No.: WO2020/008119
PCT Pub. Date: Jan. 9, 2020

(65) Prior Publication Data
US 2021/0259928 A1    Aug. 26, 2021

(30) Foreign Application Priority Data
Jul. 6, 2018 (FR) ..................... 18 56239

(51) Int. Cl.
| | | |
|---|---|---|
| A61K 8/06 | (2006.01) | |
| A61K 8/81 | (2006.01) | |
| A61Q 19/10 | (2006.01) | |
| A61K 8/92 | (2006.01) | |
| A61Q 5/02 | (2006.01) | |

(52) U.S. Cl.
CPC ............ *A61K 8/062* (2013.01); *A61K 8/8147* (2013.01); *A61K 8/8152* (2013.01); *A61K 8/8164* (2013.01); *A61K 8/8188* (2013.01); *A61K 8/922* (2013.01); *A61Q 5/02* (2013.01); *A61Q 19/10* (2013.01); *A61K 2800/48* (2013.01); *A61K 2800/5424* (2013.01); *A61K 2800/596* (2013.01); *A61K 2800/805* (2013.01)

(58) Field of Classification Search
None
See application file for complete search history.

(56) References Cited

U.S. PATENT DOCUMENTS

| | | |
|---|---|---|
| 2006/0217283 A1 | 9/2006 | De Salvert et al. |
| 2007/0238829 A1 | 10/2007 | Paul |
| 2008/0187673 A1 | 8/2008 | Standke et al. |
| 2016/0184195 A1 * | 6/2016 | Tan .......................... A61K 8/87 424/70.17 |
| 2019/0133905 A1 | 5/2019 | Heffernan et al. |

FOREIGN PATENT DOCUMENTS

| | | | | |
|---|---|---|---|---|
| EP | 1 704 852 A1 | 9/2006 | | |
| FR | 3 057 461 A1 | 4/2018 | | |
| FR | 3057461 A1 * | 4/2018 | ............. | A61K 8/062 |
| WO | WO 2006/063730 A1 | 6/2006 | | |
| WO | WO 2017/187123 A1 | 11/2017 | | |
| WO | WO-2017187123 A1 * | 11/2017 | ............. | A61K 8/463 |

OTHER PUBLICATIONS

International Search Report dated Sep. 17, 2019 in PCT/FR2019/000108 filed on Jul. 1, 2019, 2 pages.
Yurdacan et al, "Functional green-based nanomaterials towards sustainable carbon capture and sequestration" *Sustainable Materials for Transitional and Alternative Energy*, ed. Mafrettin Murat Sari, by Gulf Professional Publishing, Chapter 3, 2021, pp. 125-177.

* cited by examiner

*Primary Examiner* — Brian Gulledge
(74) *Attorney, Agent, or Firm* — Oblon, McClelland, Maier & Neustadt, L.L.P.

(57) ABSTRACT

A water-rinsable, aqueous cleansing formulation may include a cosmetic oily component. The formulation may foam and remain stable despite the presence of a cosmetic oily component, even when the oily component is present in potentially substantial amounts.

17 Claims, No Drawings

COSMETIC CLEANSING FORMULATION

This invention relates to a water-rinsable, aqueous cleansing formulation comprising a cosmetic oil component. The formulation according to the invention foams and remains stable despite the presence of a cosmetic oil component, even when the oil component is present in potentially substantial amounts.

The present invention relates to the field of cleansing formulations, more particularly compositions such as shower gels and shower creams for cleansing the skin, and shampoos for the hair. These formulations are cosmetic or dermatological formulations.

These formulations are intended to cleanse skin or hair on the human body. These formulations are then intended to be rinsed with water.

Typically, a cleansing formulation comprises water and surface-active agents that enable the formulation to foam and cleanse.

Other ingredients may be added to the formulation such as gel-forming agents that give it a gel consistency, foam boosters that make the foam more or less abundant and persistent, chelating agents that act to detach limescale, hydrating and moisturising agents that help maintain skin hydration, dyes to give the formulation an attractive colour, fragrance, vegetable extracts, and most often preservatives to prevent bacterial proliferation in the formulation. The addition of an oil component such as a cosmetic oil, often a vegetable oil for, for example nourishing, hydrating the skin and preventing the skin from drying after cleansing, is also known.

However, adding a significant amount, corresponding to at least several weight percentages, of an oil component is always a challenge for the formulator. Indeed, not only will the cosmetic oil component disrupt the foaming capacity of the cleansing formulation, but also, if the droplets are broadly distributed, the smaller droplets of the oil component will migrate to the larger ones, leading to an increase in average droplet size. This phenomenon is known as Ostwald ripening. Such a phenomenon destabilises the cleansing formulation: the oil phase separates from the aqueous phase. Thus, the oil component is no longer dispersed in the aqueous phase. This phenomenon is irreversible. Document WO 2017-187123 describes shampoo or shower gel compositions comprising insoluble agents such as exfoliating agents, encapsulation agents, or oils. Document FR 3057461 presents cosmetic or dermatological compositions in the form of oil-in-water type nano-emulsions. These compositions are formulated using a modified hydrophobic inulin polymer.

Document WO 2006-063730 describes the manufacture of a stable, high-granulometry silicone emulsion made up of a combination of organo-polysiloxanes, emulsifiers and water. Document EP 1704852 describes foaming topical compositions that are oil-in-water emulsions. These compositions comprise an oil phase dispersed in an aqueous phase comprising an emulsifier system and a foaming system containing a nonionic alkyl polyglucoside surface-active agent and an amphoteric surface-active agent. Document WO 2006-081892 presents an oil-in-water emulsion comprising functional alcoxysilanes or organoalcoxysiloxanes combined with an emulsifier and water. This emulsion can be used to render porous mineral building materials hydrophobic.

The invention proposes cleansing formulations that are stable, have good foaming capacity and comprise a cosmetic oil component at contents that can be significant.

The invention relates to a water-rinsable, aqueous cleansing formulation comprising:
a) at least one anionic copolymer A chosen among an ASE copolymer, a HASE copolymer and combinations thereof;
b) from 1 to 40% by weight, relative to the total weight of the formulation, of at least one cosmetic oil component B in the form of droplets dispersed in the aqueous phase with a polydispersity, (D90%–D10%)/D50%, of less than 1.7;
c) at least one surface-active agent C.

The aqueous cleansing formulation is intended to wash at least the skin, skin appendages or hair of a mammal, especially humans. It is then intended to be removed from the surface of the skin, skin appendages or hair by simply rinsing with water. The aqueous cleansing formulation is advantageously a shower gel or a shampoo.

In the formulation according to the invention, the cosmetic oil component B is dispersed as droplets in the aqueous phase.

According to the invention, the droplets of the cosmetic oil component B are distributed homogeneously, thereby limiting the risk of destabilisation from Ostwald ripening. In particular, the polydispersity of the droplets of the oil component B is less than 1.6, advantageously less than 1.5.

Thus, the formulation according to the invention is stable. Surprisingly, it also retains good foaming capacity regardless of the nature of the cosmetic oil component B, particularly vegetable oil, that is introduced. Foaming capacity denotes, as meant under the present invention, the capacity of a cleansing formulation to produce stable foam. Consequently, not only is the amount of foam produced evaluated, but also the stability of the foam that is formed.

The droplets of the cosmetic oil component B advantageously have a D50% less than 50 µm, more advantageously less than 30 µm, even more advantageously less than 10 µm.

The droplets of the cosmetic oil component B advantageously have a D50% greater than 0.1 µm, more advantageously greater than 0.25 µm or 0.5 µm, even more advantageously greater than 1 µm.

In particular, the droplets of the cosmetic oil component B have a D50% ranging from 0.1 to 50 µm, advantageously from 0.25 to 30 µm or from 0.5 to 30 µm, more advantageously from 1 to 10 µm.

In the formulation according to the invention, the anionic copolymer A is advantageously, at least in part, found at the interface of the droplets of the cosmetic oil component B.

Although it may comprise large amounts of cosmetic oil component B, the formulation according to the invention is stable and has an effective foaming capacity for use as a cleansing formulation, particularly as a shower gel or a shampoo.

The pH of the formulation according to the invention advantageously ranges from 5 to 12, more advantageously from 5 to 8, even more advantageously from 5 to 7, even more advantageously from 5.5 to 7, even more advantageously from 5.5 to 6.7.

The formulation according to the invention can be obtained through a method comprising the following steps:
a) preparing an oil-in-water emulsion comprising, by weight, relative to the weight of the oil-in-water emulsion:
from 0.5 to 4% of at least one anionic copolymer A chosen among an ASE copolymer, a HASE copolymer and combinations thereof,
from 20 to 70% of at least one cosmetic oil component B, q.s.p 100% water,
by adding, under stirring, at least one cosmetic oil component B to an aqueous phase (AP), having a pH greater than or equal to 6.5, comprising the anionic polymer A and water, and
b) mixing the oil-in-water emulsion obtained as a result of step a) with an aqueous composition comprising at least one surface-active agent C.

This method, particularly steps a) and b), is as described hereafter for the method according to the invention.

Before describing this method, we will first describe the various ingredients of the aqueous cleansing formulation according to the invention.

Anionic Copolymer A

The formulation according to the invention comprises at least one anionic copolymer A chosen among an ASE copolymer, a HASE copolymer and combinations thereof. This anionic copolymer A makes it possible to control, in particular to reduce, the polydispersity of the droplets of cosmetic oil component B in the aqueous phase.

ASE denotes an alkali-soluble emulsion, a carboxylated copolymer made of:
(a1) at least one anionic monomer comprising at least one polymerisable olefinic unsaturation, preferably an anionic monomer comprising at least one polymerisable olefinic unsaturation and at least one carboxylic acid group
and (a2) at least one ester of a compound derived from a carboxylic acid comprising at least one polymerisable olefinic unsaturation.

HASE denotes a hydrophobically-modified alkali-soluble emulsion, a carboxylated copolymer made from:
(a1) at least one anionic monomer comprising at least one polymerisable olefinic unsaturation, preferably an anionic monomer comprising at least one polymerisable olefinic unsaturation and at least one carboxylic acid group,
(a2) at least one ester of a compound derived from a carboxylic acid comprising at least one polymerisable olefinic unsaturation and
(a3) at least one associative hydrophobic monomer.

According to the invention, the preferred anionic copolymer A is chosen among:
an ASE copolymer prepared by polymerisation reaction:
(a1) of at least one anionic monomer comprising at least one polymerisable olefinic unsaturation, preferably an anionic monomer comprising at least one polymerisable olefinic unsaturation and at least one carboxylic acid group;
(a2) of at least one ester of a compound derived from a carboxylic acid comprising at least one polymerisable olefinic unsaturation;
(a4) optionally, of at least one monomer comprising at least one polymerisable olefinic unsaturation and a sulphonic acid or phosphoric acid group;
(a5) optionally, of at least one monomer chosen among a hydroxy($C_1$-$C_6$)-alkyl acrylate, a hydroxy($C_1$-$C_6$)-alkyl methacrylate and combinations thereof,
(a6) optionally, of at least one cross-linking monomer or of at least one monomer comprising at least two olefinic unsaturations;
a HASE copolymer prepared by polymerisation reaction:
(a1) of at least one anionic monomer comprising at least one polymerisable olefinic unsaturation, preferably an anionic monomer comprising at least one polymerisable olefinic unsaturation and at least one carboxylic acid group;
(a2) of at least one ester of a compound derived from a carboxylic acid comprising at least one polymerisable olefinic unsaturation;
(a3) of at least one associative hydrophobic monomer;
(a4) optionally, of at least one monomer comprising at least one polymerisable olefinic unsaturation and a sulphonic acid or phosphoric acid group;
(a5) optionally, of at least one monomer chosen among a hydroxy($C_1$-$C_6$)-alkyl acrylate, a hydroxy($C_1$-$C_6$)-alkyl methacrylate and combinations thereof,
(a6) optionally, of at least one cross-linking monomer or of at least one monomer comprising at least two olefinic unsaturations;
and combinations thereof.

Advantageously, at least one, more advantageously several or all, of the following conditions are met:
the anionic monomer (a1) is independently chosen among acrylic acid, methacrylic acid, maleic acid, maleic anhydride, itaconic acid, crotonic acid, an acrylic acid salt, a methacrylic acid salt, a maleic acid salt, a maleic anhydride salt, an itaconic acid salt, a crotonic acid salt and combinations thereof, much more preferentially acrylic acid or methacrylic acid;
the monomer (a2) is independently chosen among an ester of a compound derived from an acid chosen among acrylic acid, methacrylic acid, maleic acid, maleic anhydride, itaconic acid and crotonic acid, preferably an acrylic acid ester or a methacrylic acid ester, preferably chosen among methyl acrylate, ethyl acrylate, propyl acrylate, butyl acrylate, ethyl hexyl acrylate, methyl methacrylate, ethyl methacrylate, propyl methacrylate, butyl methacrylate, ethyl hexyl methacrylate, and combinations thereof,
the monomer (a3) is a compound of formula (I):

$$R^1\text{-}(EO)_m\text{—}(PO)_n\text{—}R^2 \qquad (I)$$

wherein:
m and n, identical or different, independently represent 0 or an integer or decimal less than 150, m or n is different from 0,
EO independently represents a $CH_2CH_2O$ group,
PO independently represents a group chosen among $CH(CH_3)CH_2O$ and $CH_2CH(CH_3)O$,
$R^1$ represents a group comprising at least one polymerisable olefinic unsaturation, preferably an acrylate group or a methacrylate group and
$R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group;
monomer (a4) is a compound independently chosen among 2-acrylamido-2-methylpropane sulphonic acid, ethoxymethacrylate sulphonic acid, sodium methallyl sulphonate, styrene sulphonate hydroxyethyl acrylate phosphate, hydroxypropyl acrylate phosphate, hydroxyethylhexyl acrylate phosphate, hydroxyethyl methacrylate phosphate, hydroxypropyl methacrylate phosphate, hydroxyethylhexyl methacrylate phosphate, their salts and combinations thereof;
the monomer (a5) is a compound independently chosen among hydroxyethyl acrylate, hydroxypropyl acrylate, hydroxyethylhexyl acrylate, hydroxyethyl methacrylate, hydroxypropyl methacrylate, hydroxyethylhexyl methacrylate.

The preferred ASE anionic copolymers are prepared by polymerisation reaction:
- (a1) of at least one anionic monomer comprising at least one polymerisable olefinic unsaturation, preferably an anionic monomer comprising at least one polymerisable olefinic unsaturation and at least one carboxylic acid group, preferably the anionic monomer is independently chosen among acrylic acid, methacrylic acid, maleic acid, maleic anhydride, itaconic acid, crotonic acid, an acrylic acid salt, a methacrylic acid salt, a maleic acid salt, a maleic anhydride salt, an itaconic acid salt, a crotonic acid salt and combinations thereof, much more preferentially acrylic acid or methacrylic acid and
- (a2) of at least one ester of a compound derived from an acid independently chosen among acrylic acid, methacrylic acid, maleic acid, maleic anhydride, itaconic acid and crotonic acid, preferably an acrylic acid ester or a methacrylic acid ester, preferably chosen among methyl acrylate, ethyl acrylate, propyl acrylate, butyl acrylate, ethyl hexyl acrylate, methyl methacrylate, ethyl methacrylate, propyl methacrylate, butyl methacrylate, ethyl hexyl methacrylate and combinations thereof.

Also preferably, the HASE anionic copolymers are prepared by a polymerisation reaction that also uses:
- (a3) at least one compound of formula (I):

$$R^1\text{-}(EO)_m\text{—}(PO)_n\text{—}R^2 \quad (I)$$

wherein:
- m and n, identical or different, independently represent 0 or an integer or decimal less than 150, m or n is different from 0,
- EO independently represents a $CH_2CH_2O$ group,
- PO independently represents a group chosen among $CH(CH_3)CH_2O$ and $CH_2CH(CH_3)O$,
- $R^1$ represents a group comprising at least one polymerisable olefinic unsaturation, preferably an acrylate group or a methacrylate group and
- $R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group.

Also preferably, the ASE or HASE anionic copolymers are prepared by a polymerisation reaction that also uses:
- (a4) at least one compound independently chosen among 2-acrylamido-2-methylpropane sulphonic acid, ethoxymethacrylate sulphonic acid, sodium methallyl sulphonate, styrene sulphonate, hydroxyethyl acrylate phosphate, hydroxypropyl acrylate phosphate, hydroxyethylhexyl acrylate phosphate, hydroxyethyl methacrylate phosphate, hydroxypropyl methacrylate phosphate, hydroxyethylhexyl methacrylate phosphate, their salts and combinations thereof.

Also preferably, the ASE or HASE anionic copolymers are prepared by a polymerisation reaction that also uses:
- (a5) at least one compound independently chosen among hydroxyethyl acrylate, hydroxypropyl acrylate, hydroxyethylhexyl acrylate, hydroxyethyl methacrylate, hydroxypropyl methacrylate, hydroxyethylhexyl methacrylate.

Also preferably, the ASE or HASE anionic copolymers are prepared by a polymerisation reaction that also uses:
- (a6) at least one cross-linking monomer or at least one monomer comprising at least two olefinic unsaturations.

Monomer (a6) may also, for example, be independently chosen among di(meth)acrylates such as polyalkylene glycol di(meth)acrylate, in particular polypropylene glycol di(meth)acrylate, ethylene glycol di(meth)acrylate, polyethylene glycol di(meth)acrylate, triethylene glycol di(meth)acrylate, 1,3-butylene glycol di(meth)acrylate, 1,6-butylene glycol di(meth)acrylate, 1,6-hexanediol di(meth)acrylate, neopentyl glycol di(meth)acrylate, 1,9-nonanediol di(meth)acrylate, but also 2,2'-bis(4-(acryloxy-propyloxyphenyl))propane, 2,2'-bis(4-(acryloxydiethoxy-phenyl))propane and zinc acrylate; tri(meth)acrylate compounds such as trimethylolpropane tri(meth)acrylate and ethoxylated trimethylolpropane tri(meth)acrylate, trimethylolethane tri(meth)acrylate, pentaerythritol tri(meth)acrylate and tetramethylolmethane tri(meth)acrylate; tetra(meth)acrylate compounds such as di-trimethylolpropane tetra(meth)acrylate, tetramethylolmethane tetra(meth)acrylate and pentaerythritol tetra(meth)acrylate; hexa(meth)acrylate compounds such as dipentaerythritol hexa(meth)acrylate; penta(meth)acrylate compounds such as dipentaerythritol penta(meth)acrylate; allyl compounds such as allyl (meth)acrylate, diallyl phthalate, diallyl itaconate, diallyl fumarate, diallyl maleate; polyallyl sucrose ethers with from 2 to 8 groups per molecule, pentaerythritol polyallyl ethers such as pentaerythritol diallyl ether, pentaerythritol triallyl ether and pentaerythritol tetraallyl ether; trimethylolpropane polyallyl ethers such as trimethylolpropane diallyl ether and trimethylolpropane triallyl ether. Other polyunsaturated compounds include divinyl glycol, divinyl benzene, divinylcyclohexyl and methylenebisacrylamide.

Monomer (a6) can also be prepared by an esterification reaction of a polyol with an unsaturated anhydride such as acrylic anhydride, methacrylic anhydride, maleic anhydride, or itaconic anhydride. To obtain monomer (a6), compounds independently chosen among polyhaloalkanols may also be used such as 1,3-dichloroisopropanol and 1,3-dibromoisopropanol; haloepoxyalkanes such as epichlorohydrin, epibromohydrin, 2-methyl epichlorohydrin and epiiodohydrin; polyglycidyl ethers such as 1,4-butanediol diglycidyl ether, glycerin-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ether, bisphenol A-epichlorohydrin epoxy resin and mixtures thereof.

Monomer (a6) can also be chosen among the trifunctional cross-linking agents. This may be in particular trimethylolpropane tri(meth)acrylate (TMPTA) or ethoxylate trimethylolpropane tri(meth)acrylate (such as TMPTA 3EO).

Monomer (a6) can also be chosen among trimethylolpropane tri(meth)acrylate, ethoxylated trimethylolpropane tri(meth)acrylate, ethylene glycol di(meth)ethylacrylate, methylenebisacrylamide, diallyl phthalate, diallyl maleate and mixtures thereof.

Monomer (a6) can also be a mixture of two separate monomers, such as EGDCPEA (ethylene glycol dicyclopentenyl ether acrylate) and TMPTA or EGDCPEA and TMPTA 3EO or even EGDCPEMA (ethylene glycol dicyclopentenyl ether methacrylate) and TMPTA or EGDCPEMA and TMPTA 3EO.

According to the invention, monomer (a6) is preferably chosen among trimethylolpropane trimethacrylate, trimethylolpropane triacrylate, ethoxylated trimethylolpropane trimethacrylate, ethoxylated trimethylolpropane triacrylate, ethylene glycol dimethacrylate, ethylene glycol diacrylate, methylenebisacrylamide, diallyl phthalate, diallyl maleate and mixtures thereof.

The particularly preferred ASE anionic copolymers according to the invention are prepared by a polymerisation reaction that uses:
(a1) acrylic acid, methacrylic acid, or acrylic acid and methacrylic acid and
(a2) methyl acrylate, methyl methacrylate, ethyl acrylate, ethyl methacrylate and combinations thereof.

The particularly preferred HASE anionic copolymers according to the invention are prepared by a polymerisation reaction that uses:
(a1) acrylic acid, methacrylic acid, or acrylic acid and methacrylic acid,
(a2) methyl acrylate, methyl methacrylate, ethyl acrylate, ethyl methacrylate and combinations thereof,
(a3) at least one compound of formula (I):

$$R^1\text{-}(EO)_m\text{---}(PO)_n\text{---}R^2 \quad (I)$$

wherein:
m and n, identical or different, independently represent 0 or an integer or decimal less than 150, m or n is different from 0,
EO independently represents a $CH_2CH_2O$ group,
PO independently represents a group chosen among $CH(CH_3)CH_2O$ and $CH_2CH(CH_3)O$,
$R^1$ represents an acrylate group or a methacrylate group and
$R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group.

Other particularly preferred ASE anionic copolymers according to the invention are prepared by a polymerisation reaction that uses:
(a1) acrylic acid, methacrylic acid, or acrylic acid and methacrylic acid,
(a2) methyl acrylate, methyl methacrylate, ethyl acrylate, ethyl methacrylate and combinations thereof,
(a4) 2-acrylamido-2-methylpropane sulphonic acid.

Other particularly preferred HASE anionic copolymers according to the invention are prepared by a polymerisation reaction that also uses:
(a1) acrylic acid, methacrylic acid, or acrylic acid and methacrylic acid,
(a2) methyl acrylate, methyl methacrylate, ethyl acrylate, ethyl methacrylate and combinations thereof,
(a3) at least one compound of formula (I):

$$R^1\text{-}(EO)_m\text{---}(PO)_n\text{---}R^2 \quad (I)$$

wherein:
m and n, identical or different, independently represent 0 or an integer or decimal less than 150, m or n is different from 0,
EO independently represents a $CH_2CH_2O$ group,
PO independently represents a group chosen among $CH(CH_3)CH_2O$ and $CH_2CH(CH_3)O$,
$R^1$ represents an acrylate group or a methacrylate group and
$R^2$ represents a straight or branched $C_6$-$C_{40}$-alkyl group, a phenyl group, a polyphenyl group, preferably a straight or branched $C_{10}$-$C_{30}$-alkyl group, more preferentially a straight or branched $C_{12}$-$C_{22}$-alkyl group, or a group comprising 2 to 5 phenyls or a tristyrylphenyl group or a pentastyrylcumylphenyl group and
(a4) 2-acrylamido-2-methylpropane sulphonic acid.

When preparing the anionic copolymer A used according to the invention at least one chain transfer agent can be used, preferably chosen among the mercaptan compounds, particularly mercaptan compounds comprising at least four carbon atoms such as butyl mercaptan, n-octyl mercaptan, n-dodecyl mercaptan, tert-dodecyl mercaptan, iso-octylmercaptopropionate.

The formulation according to the invention advantageously comprises from 0.007% to 8% by weight, relative to its total weight, of anionic copolymer A. The formulation also advantageously comprises from 0.036% to 7% by weight, more advantageously from 0.050% to 6% by weight, relative to its total weight, of anionic copolymer A. The formulation also advantageously comprises from 0.007% to 7% by weight, more advantageously from 0.007% to 6% by weight, relative to its total weight, of anionic copolymer A. The formulation also advantageously comprises from 0.036% to 8% by weight, more advantageously from 0.036% to 6% by weight, relative to its total weight, of anionic copolymer A. The formulation also advantageously comprises from 0.050% to 7% by weight, more advantageously from 0.050% to 6% by weight, relative to its total weight, of anionic copolymer A.

Cosmetic Oil Component B

The cosmetic oil component B is an oil component suitable for cosmetic or dermatological use.

The oil component B can be chosen among an inorganic fatty substance, a synthetic fatty substance, a vegetable fatty substance, an animal fatty substance and combinations thereof.

In particular, oil component B can be chosen among a fatty acid, a fatty alcohol, a butter, a wax, an oil, an unsaponifiable compound, a terpene, a sterol and combinations thereof. Examples of wax include in particular beeswax.

The oil can be chosen among an inorganic oil, an animal oil, a vegetable oil, a synthetic oil, a siliconised oil, a fluorinated oil and combinations thereof, preferably a vegetable oil. Preferably, the oil is chosen among an inorganic oil, an animal oil, a vegetable oil, a synthetic oil, a fluorinated oil and combinations thereof, preferably a vegetable oil. Examples of inorganic oils include in particular paraffin oil, petrolatum oil, inorganic oils with a boiling point ranging from 300 to 400° C.

Examples of animal oils include in particular squalene, squalane, perhydrosqualene. Examples of synthetic oils include in particular hydrogenated polyisobutene, fatty acid esters such as purcellin oil, butyl myristate, isopropyl myristate, cetyl myristate, isopropyl palmitate, butyl stearate, hexadecyl stearate, isopropyl stearate, octyl stearate, isocetyl sterate, decyl oleate, hexyl laurate, propylene glycol dicaprylate, esters derived from lanolic acid such as disopropyl lanolate, isocetyl lanolate, acetylglycerides, alcohol octanoates, polyalcohol octanoates, alcohol decanoates, polyalcohol decanoates, in particular glycol octanoates, glycerol octanoates, glycol decanoates, glycerol decanoates, alcohol ricinoleates, polyalcohol ricinoleates and combinations thereof.

Examples of siliconised oils include in particular cyclomethicones, low molecular weight polydimethylsiloxanes or silicone oils, high molecular weight polydimethylsiloxanes or silicone gums, polymethylsiloxanes, dimethiconols, poly(dimethylphenyl siloxanes), low molecular weight siloxanols, high molecular weight siloxanols, trimethylsiloxysilicates and combinations thereof.

Examples of fluorinated oils include in particular fluorinated perfluoroethers, fluorinated silicones and combinations thereof.

Examples of vegetable oils include in particular sweet almond oil, calophyllum oil, palm oil, apricot kernel oil, avocado oil, jojoba oil, olive oil, sunflower oil, castor oil, sesame seed oil, seed oils, shea butter liquid fraction and combinations thereof.

Unsaponifiable compounds are advantageously derived from vegetable oils.

Terpenes include, in particular, monoterpenes, sesquiterpenes, diterpenes, sesterterpenes, triterpenes, tetraterpenes and polyterpenes.

The sterol is advantageously a phytosterol.

The cosmetic oil component B is preferably chosen among a vegetable oil, an unsaponifiable compound derived from a vegetable oil, a synthetic oil and combinations thereof. The cosmetic oil component B is more particularly a vegetable oil.

The formulation according to the invention advantageously comprises from 5 to 35% by weight, more advantageously from 7 to 30% by weight, relative to its total weight, of cosmetic oil component B. The formulation also advantageously comprises from 1 to 35% by weight, more advantageously from 1 to 30% by weight, relative to its total weight, of cosmetic oil component B. The formulation also advantageously comprises from 5 to 35% by weight, more advantageously from 7 to 30% by weight, relative to its total weight, of cosmetic oil component B. The formulation also advantageously comprises from 5 to 40% by weight, more advantageously from 5 to 30% by weight, relative to its total weight, of cosmetic oil component B. The formulation also advantageously comprises from 7 to 40% by weight, more advantageously from 7 to 35% by weight, relative to its total weight, of cosmetic oil component B.

Surface-Active Agent C

Surface-active agent refers to an ingredient that reduces surface tension and promotes skin cleansing. Many surface-active compounds also act as emulsifying agents or foaming agents. There are four main categories of surface-active agents: cationic, anionic, amphoteric and nonionic. Amphoteric surface-active agents and nonionic surface-active agents are generally best tolerated by the epidermis.

The surface-active agents C include, in particular, ammonium laureth sulphate; ammonium lauryl sulphate; caprylyl/capryl glucoside; cetyl betaine; cocamidopropyl betaine;
- coco-betaine; coco-glucoside; decyl glucoside; disodium cocoamphodiacetate; disodium laureth sulphosuccinate; disodium lauryl sulphosuccinate; disodium stearoyl glutamate; glycol stearate; lauramidopropyl betaine; PEG-100 stearate; potassium cetyl phosphate; sodium cocoamphoacetate; sodium cocoyl isethionate; sodium laureth sulfate; sodium lauryl sulfate; sodium palm kernelate; sodium methyl cocoyl laurate; alpha olefin sulphonates such as sodium $C_{14}$-$C_{16}$ alpha olefin sulphonate; sodium lauroyl methyl isethionate; cocamidopropyl hydrosultaine; sodium lauroyl sarcosinate; sodium cocoyl glutamate; sodium cocoyl glycinate; sodium lauroyl lactylate; alkyl glucoside; alkyl polyglucoside; caprylic/capric glucoside lauryl ether; polysorbates such as polysorbate 80, polysorbate 20; sodium methyl sulpholaurate; sodium lauryl sulfoacetate; disodium sulfolaurate; soaps, which are fatty acid salts, of general formula RCOOM (R=long hydrocarbon chain with more than 10 carbon atoms, M=a metal, an alkali-metal or an organic base). Depending on the nature of the M group, there are alkali-metal soaps ($Na^+$, $K^+$, $NH_4^+$ soaps), metal soaps (particularly of calcium) and organic soaps (for example, triethanolamine soap, including triethanolamine stearate) and combinations thereof. Advantageously, the surface-active agent C is chosen among an anionic surface-active agent, an amphoteric surface-active agent, a nonionic surface-active agent and combinations thereof.

Advantageously, the formulation comprises from 2 to 25% by weight, relative to its total weight, of surface-active agent C.

Suspensivant Agent

Preferably, the formulation also comprises at least one suspensivant agent. This suspensivant agent improves the stability of the droplets of the oil component in the aqueous formulation by preventing their migration due to the difference in density between the droplets of the oil component and the aqueous phase.

This migration phenomenon is not to be confused with the stability relating to the Ostwald ripening phenomenon. When stability is lost due to Ostwald ripening, the droplets irreversibly combine until an oil phase is formed that can no longer be considered to be dispersed in the aqueous phase. Moreover, this phenomenon is irreversible, and agitation alone does not enable this oil phase to be dispersed in the aqueous phase.

When stability is lost due to the migration of the droplets of the oil component, the oil phase remains dispersed in the aqueous phase. Moreover, this state is reversible. A simple manual agitation of the container containing the formulation enables a homogeneous dispersion to be restored.

The suspensivant agent can be chosen among a cross-linked anionic copolymer, a carbomer, a xanthan gum and combinations thereof. Preferably, the suspensivant agent is a cross-linked anionic copolymer. Examples of xanthan gum include, in particular, the following commercial products: Rheocare XGN (BASF), Rhodicare 80 Pharma (Solvay), Rhodicare 200 Pharma (Solvay).

The cross-linked anionic copolymer is advantageously a cross-linked ASE or cross-linked HASE copolymer. Advantageously, it is a cross-linked ASE copolymer obtained by polymerisation of at least one monomer (a1), of at least one monomer (a2) and of at least one monomer (a6). The cross-linked ASE copolymer can also be obtained by polymerisation of the monomers (a1), (a2) and (a6) with one or more monomers chosen among a monomer (a4), a monomer (a5) and combinations thereof. Advantageously, it is a cross-linked HASE copolymer obtained by polymerisation of at least one monomer (a1), of at least one monomer (a2), of at least one monomer (a3) and of at least one monomer (a6). The cross-linked HASE copolymer can also be obtained by polymerisation of monomers (a1), (a2), (a3) and (a6) with one or more monomers chosen among a monomer (a4), a monomer (a5) and combinations thereof.

The monomers (a1), (a2), (a3), (a4), (a5) and (a6) are as defined for the anionic copolymer A according to the invention.

Examples of cross-linked ASE or cross linked HASE copolymers include, in particular, the following commercial products:
- copolymer acrylates: Rheostyl 100 (Coatex), Carbopol Aqua SF-1 (Lubrizol), Aculyn 33 (Dow), Synthalen W 400 (3V Sigma), Viscolam MAC 10 (Lamberti), Emul 34U (Tinci), Acecare 30KC (KCl), Rheocare TTA (BASF), Surfathix N (Ashland), Rheostyl 85L (Coatex), Aculyn Excel (Dow), acrylates/palmeth-25 acrylate copolymers: Synthalen W 2000 (3V Sigma),
polyacrylate-33: Rheomer 33 (Solvay),
acrylates crosspolymer-4: Carbopol Aqua SF-2 (Lubrizol),
acrylates/C10-30 Alkyl Acrylate Crosspolymer: Ultrez 20 (Lubrizol),
acrylates/Beheneth-25 Methacrylate Copolymer: Low pH Rheomer,
acrylates/Beheneth-25 Methacrylate/HEMA Crosspolymer: Carbopol SMART 1000 (Lubrizol), Carbopol SMART 2000 (Lubrizol), Carbopol SMART 3000 (Lubrizol),
acrylates/Steareth-20 Methacrylate Crosspolymer: Aculyn 88 (Dow).

This additional ASE or HASE anionic copolymer, which is cross-linked, acts as a suspensivant.

Other Ingredients

The formulation according to the invention may also comprise any other ingredient typically introduced in a cleansing formulation, particularly in a shower gel or a shampoo. In particular, the formulation according to the invention also comprises one or more of the following ingredients:
- at least one cationic polymer chosen among Polyquaternium-1 to Polyquaternium-47 and quaternised guars;
- at least one preservative;
- at least one solubilising agent, such as fatty acids, fatty alcohols, collagen or protein hydrolysates and combinations thereof. A solubilising agent is an ingredient that promotes the formation of intimate mixtures between non-mixable liquids (such as water and fragrance);
- at least one active hydrating and moistening ingredient such as glycerol (INCI name: Glycerin);
- at least one vegetable extract;
- at least one active emollient ingredient;
- at least one active softening ingredient;
- at least one active soothing ingredient;
- at least one dye;
- at least one formation agent;
- at least one foam booster;
- at least one chelation agent;
- fragrance.

METHOD ACCORDING TO THE INVENTION

The invention also relates to a method for preparing a formulation according to the invention, comprising the following steps:
a) preparing an oil-in-water emulsion comprising, by weight, relative to the weight of the oil-in-water emulsion:
   from 0.5 to 4% of at least one anionic copolymer A chosen among an ASE copolymer, a HASE copolymer and combinations thereof,
   from 20 to 70% of at least one cosmetic oil component B,
   q.s.p 100% water,
   by adding, under stirring, at least one cosmetic oil component B to an aqueous phase (AP) having a pH greater than or equal to 6.5, comprising the anionic copolymer A and water and
b) mixing the oil-in-water emulsion obtained as a result of step a) with an aqueous composition comprising at least one surface-active agent C.

The oil-in-water emulsion prepared in step a) advantageously comprises from 20 to 50% by weight, relative to the weight of the oil-in-water emulsion, of cosmetic oil component B.

The oil-in-water emulsion prepared in step a) advantageously comprises from 0.05 to 2% by weight, more advantageously from 0.05 to 1% by weight, relative to the weight of the oil-in-water emulsion, of said anionic copolymer A.

The oil-in-water emulsion prepared in step a) advantageously comprises from 1 to 4% by weight, more advantageously from 1 to 2% by weight, relative to the weight of the oil-in-water emulsion, of said anionic copolymer A.

The oil-in-water emulsion prepared in step a) advantageously comprises from 2 to 4% by weight, relative to the weight of the oil-in-water emulsion, of said anionic copolymer A. The ratio (cosmetic oil component B)/(anionic copolymer A) varies advantageously from 5 to 140, more advantageously from 10 to 140, even more advantageously from 20 to 140.

The ratio (cosmetic oil component B)/(anionic copolymer A) varies advantageously from 5 to 70, more advantageously from 10 to 70.

The ratio (cosmetic oil component B)/(anionic copolymer A) varies advantageously from 5 to 35.

Advantageously, the aqueous phase (AP) also comprises a base. Preferably, it is an inorganic base, in particular a base chosen among NaOH, KOH, ammonium derivatives, ammonia and combinations thereof. Also preferably, it is a base chosen among the amine bases, for example triethanolamine, aminomethyl propanol or 2-amino-2-methyl-propanol (AMP) and combinations thereof.

The method according to the invention also advantageously uses an aqueous phase (AP) that has a pH greater than 6.5. The method according to the invention also advantageously uses an aqueous phase (AP) that has a pH of less than 12.

More advantageously, the method according to the invention uses an aqueous phase (AP) that has a pH ranging from 6.5 to 12, advantageously ranging from 6.5 to 11, advantageously ranging from 7 to 12.

The aqueous phase (AP) is advantageous prepared by a method comprising the following steps:
(a-i) mixing at least one anionic copolymer A chosen among an ASE copolymer, a HASE copolymer and combinations thereof and water; then
(a-ii) adjusting the pH of the mixture obtained at step (a-ii) to a value greater than or equal to 6.5.

Generally according to the invention, the aqueous phase (AP) does not comprise a surface-active agent or it comprises a small amount of surface-active agent, preferably nonionic. The amount of surface-active agent, preferably nonionic, can therefore range from 0.05 to 2% by weight or from 0.05 to 1% by weight, of the weight of the aqueous phase (AP).

Advantageously according to the invention, the preparation temperature is lower than the boiling point of the hydrophilic phase and lower than the boiling point of the lipophilic phase. Also advantageously according to the invention, the preparation temperature is higher than the melting point of the hydrophilic phase and higher than the melting point of the lipophilic phase.

Preferably, the preparation temperature is lower than the boiling point of the hydrophilic phase and lower than the boiling point of the lipophilic phase while being higher than the melting point of the hydrophilic phase and higher than the melting point of the lipophilic phase.

The method according to the invention comprises the addition of the cosmetic oil component B into the aqueous phase (AP) under agitation, advantageously at a speed ranging from 200 to 10,000 rpm, more advantageously from 500 to 5,000 rpm. Any means of agitation can be used. For example, the device used is a blender, in particular a VMI Rayneri blender or an Ika blender.

After step a) and prior to step b), additional steps may also be used in the method according to the invention.

Thus, advantageously, the method according to the invention may also comprise neutralisation of the oil-in-water emulsion obtained as a result of step a). Preferably, neutralisation is achieved by means of at least one compound chosen among NaOH, KOH, ammonium derivatives, ammonia, amine bases, for example triethanolamine, aminomethyl propanol or 2-amino-2-methyl-propanol (AMP) and combinations thereof. Also advantageously, the method according to the invention may also comprise partial coacervation of the anionic copolymer A. Preferably, the partial coacervation of the anionic copolymer A is achieved by reducing the pH of the oil-in-water emulsion obtained as a result of step a), for example by reducing the pH to a value less than 6.5. The pH can be reduced by means of an acid compound, in particular by means of least one organic or inorganic acid compound, in particular an acid compound chosen among phosphoric acid, citric acid, glucono-lactone, lactic acid, salicylic acid, glycolic acid, ascorbic acid, glutamic acid, hydrochloric acid, acetic acid, D-gluconic acid, sulphonic acid, methanesulphonic acid, benzimidazole sulphonic acid, tartaric acid, 4-aminobenzoic acid, benzoic acid, sorbic acid, phenyl benzimidazole sulphonic acid, benzylidene camphor sulphonic acid, terephthalylidene dicamphor sulphonic acid.

Also preferably, partial coacervation of anionic copolymer A is achieved by increasing the ionic strength of the oil-in-water emulsion obtained as a result of step a). The ionic strength of the oil-in-water emulsion obtained as a result of step a) can be increased by adding at least one ionised compound or at least one salt, particularly NaCl, KCl, $MgCl_2$, $CaCl_2$, $MgSO_4$, $CaSO_4$.

Also preferably, partial coacervation of the anionic copolymer A is achieved by reducing the solubility of the anionic copolymer in the hydrophilic phase. The solubility can be reduced by adding at least one cationic polymer, in particular a cationic polymer chosen among polyquaternium 1 to polyquaterium 47 and quaternised guars, in particular guar hydroxypropyltrimonium chloride, polydiallyldimethylammonium chloride (polyDADMAC or polyDDA), poly-2-(methacryloyloxy)ethyl-trimethylammonium chloride (polyMAD quat).

The method according to the invention can combine any of these additional steps. For example, the method according to the invention may also comprise neutralisation of the oil-in-water emulsion obtained as a result of step a) and the partial coacervation of the anionic copolymer.

The method according to the invention may also comprise a step (a') for adjusting the pH of the oil-in-water emulsion obtained as a result of step a) to a pH ranging from 5 to 12, advantageously from 5 to 8, more advantageously from 5 to 7, even more advantageously from 5.5 to 6.7.

Preferably, step (a') takes place before step b).

The resulting oil-in-water emulsion is mixed, in step b), with an aqueous composition comprising at least one surface-active agent C.

Preferably, step b) comprises a step in which the pH of the formulation obtained is adjusted to a pH ranging from 5 to 12.

Step b) advantageously comprises the following successive steps:
(b-i) mixing the oil-in-water emulsion obtained as a result of step a), as applicable as a result of step (a'), with water, then
(b-ii) adding at least one surface-active agent, then
(b-iii) adjusting the pH of the formulation obtained as a result of step (b-ii) to a pH ranging from 5 to 12, advantageously from 5 to 8, more advantageously from 5 to 7, even more advantageously from 5.5 to 6.7.

The amount of oil-in-water emulsion added is chosen based on the oil component B content desired in the final formulation. Thus, advantageously, all of the cosmetic oil component B present in the formulation obtained by the method according to the invention is achieved by adding the oil-in-water emulsion obtained as a result of step a).

As previously described, different ingredients that are typically used in a cleansing formulation can be added, particularly to a shower gel or a shampoo. These ingredients may be present or added in steps (b1) or (b2). They can also be added in an additional step after step (b2) and prior to step (b3).

The formulation obtained by the method according to the invention comprises from 1 to 40% by weight, relative to the total weight of the formulation, of at least one cosmetic oil component B in the form of droplets dispersed in the aqueous phase with a polydispersity, (D90%–D10%)/D50%, advantageously less than 1.7, more advantageously less than 1.6, even more advantageously less than 1.5.

In the formulation obtained by the method according to the invention, the D10%, D50% and D90% of the droplets of a cosmetic oil component B are as defined for the formulation according to the invention.

The formulation obtained by the method according to the invention is stable and retains good foaming capacity.

The invention also relates to a cleansing formulation that can be obtained by the method according to the invention, wherein the cosmetic oil component B is in the form of droplets dispersed in the aqueous phase and having a polydispersity, (D90%–D10%)/D50%, less than 1.7, advantageously less than 1.6, more advantageously less than 1.5.

Protocols and Measures
Evaluation of the Foam Volume and Stability
Equipment
1 Rayneri stirrer
1 40 mm notched blade
1 125 mL tall beaker
1 thermoregulated hot plate
1 fine point marker
2 timers
magnetic bar
1 scale
Raw water
Osmosis-purified water
Hard Water Test at 29° C.
Weigh 0.28 g of surface-active agent in a 125 mL tall beaker and fill up to 100 g with raw water.
Thus, for a formulation comprising 12% by weight of surface-active agent, weigh 0.28/0.012=23.3 g of formulation.
In the examples, the surface-active agents are sodium laureth sulphate (SLES) and cocoamidopropyl betaine (CAPB). In the examples, the hydrotimetric titre of the raw water is 38° TH.
Stir with magnetic stirrer and heat to 29° C. on a hot plate.
Creating the Foam
Place in the Rayneri stirrer using a notched blade.

Start stirring and bring to 2,500 rpm and maintain this speed for 60 seconds.
Stop the stirring.
Measuring the Foam Volume
30 seconds after the stirring has stopped, without shaking the beaker, mark the foam limits (high and low) on the beaker (outer sides).
4 minutes after the stirring has stopped, without shaking the beaker, mark the foam limits (high and low) on the beaker (outer sides).
Empty and clean the beaker.
Add osmosis-purified water up to the low mark, let settle for 30 seconds, weigh, then add more water up to the high mark, let settle for 30 seconds, and weigh.
Empty the beaker and add osmosis-purified water up to the low mark, let settle for 4 minutes, weigh, then add more water up to the high mark, let settle for 4 minutes, and weigh.
The foam volume after settling for 30 seconds, called volume at 30 seconds, and after settling for 4 minutes, called volume at 4 minutes, will be calculated by the difference between the top line weighing for 30 seconds, respectively for 4 minutes, and the bottom line weighing for 30 seconds, respectively for 4 minutes. For osmosis-purified water, 1 mg corresponding to 1 mL, the foam volume will be expressed in mL.
Foam Stability Calculation
Calculate the ratio between the volume at 30 seconds and the volume at 4 minutes.
Particle Size and Polydispersity
To measure the size distribution of the dispersed cosmetic oil droplets (D10, D50 or D90 in %) within the aqueous phase, a Malvern Mastersizer 2000 instrument is used.
D10% is the size for which 10% of the particle volume has a size that is smaller than this particular value.
D50% is the size for which 50% of the particle volume has a size that is smaller than this particular value.
D90% is the size for which 90% of the particle volume has a size that is smaller than this particular value.
Polydispersity is calculated using the D10%, D50% and D90% values measured.
Polydispersity is the result of (D90%–D10%)/D50%.
Brookfield Viscosity
Instrument: Brookfield LV Type Viscometer
Measurement conditions: 6 rpms, 25° C.
Stability
Equipment: heat chamber at 50° C.
If a loss of homogeneity of the sample is visually observed over the month of storage at 50° C., the formulation is considered non stable.

EXAMPLES

Raw Materials Anionic copolymer A: see method of preparation
Rhodasurf® ID 030, Solvay: ethoxylated fatty acid, CAS #: 26183-52-8
Fancryl 512-AS, Hitachi Chemical: Dicyclopentenyl acrylate, CAS #: 65983-31-5
SLES=sodium laureth sulphate (Texapon NSO UP, BASF)
CAPB=cocoamidopropyl betaine (Dehyton PK 45, BASF)
PQ-7=polyquaternium-7 (Salecare super 7 AT 1, BASF)
Sweet almond oil=oil Dulcis amygdalus prunus, CAS #: 8007-69-0/90320-37-9
Sesame seed oil=oil Sesamum Indicum, CAS #: 8008-74-0
Carbopol® Ultrez 20, Lubrizol=Acrylates/C10-30 Alkyl Acrylate Crosspolymer
Emulium Delta, Gattefossé=Cetyl Alcohol (and) Glyceryl Stearate (and) PEG-75 Stearate (and) Ceteth-20 (and) Steareth-20
Rheostyl™ 100, Coatex=acrylates copolymer
Phenoxyethanol, CAS #122-99-6
sodium hydroxide NaOH.
Anionic Copolymer A—Preparation Method
In a 1 L reactor under stirring and heated using an oil bath, mixture 1 is prepared by introducing deionised water and sodium lauryl sulphate (SLS) and optionally an ethoxylated fatty acid (Rhodasurf® ID 030).
A mixture 2, called a monomer premixture, comprising deionised water, is prepared in a beaker:
Methacrylic Acid (MAA),
Ethyl Acrylate (EA),
optionally a cross-linked monomer (Fancryl 512-AS),
sodium lauryl sulphate (SLS),
optionally an associative hydrophobic monomer, branched $C_{16}$-alkyl (EO)25-methacrylate obtained from a Guerbet reaction or straight $C_{12}$-alkyl (EO)23 methacrylate,
optionally n-dodecylmercaptan.
This premixture is stirred to form a monomer mixture.
An initiator solution 1 is prepared comprising ammonium persulphate and deionised water. Optionally, an initiator solution 2 is prepared comprising ammonium persulphate and deionised water. All reagents and amounts used are listed in Table 1.
In the reactor heated to the polymerisation temperature of ±1° C., the initiator solution 1 is injected, if applicable at the same time the initiator solution 2, then the monomer premixture for 2 hours (for CA3 in Table 1, the initiator solution 1 and the monomer premixture are injected in parallel for 2 hours and 30 minutes). The preparation is cooked for 30 minutes at the polymerisation temperature. The mixture is then cooled to room temperature.
The polymers according to the invention were prepared under these conditions by varying the monomer compositions of the monomer premixtures. The compositions of the copolymers obtained are listed in Table 1.

TABLE 1

| | Anionic Copolymer | | | |
|---|---|---|---|---|
| | Amount (g) | CA1 | CA2 | CA3 |
| Mixture 1 | Deionised water | 474.6 | 468.0 | 476.5 |
| | SLES | 6.5 | 6.4 | 0.3 |
| | Rhodasurf® ID 030 | 5.4 | 0 | 0 |
| | AMPS 2405 50% | 5.3 | 8.0 | 0 |
| Premixture | Deionised water | 140.7 | 142.3 | 93.1 |
| | SLES | 2.3 | 2.2 | 3.1 |
| | MAA | 108.6 | 101.8 | 105.9 |
| | EA | 158.1 | 150.1 | 200.2 |
| | Fancryl 512-AS cross-linking monomer | 0 | 0 | 0.6 |
| | Straight C12-alkyl (EO)23 methacrylate | 0 | 34.4 | 0 |
| | Branched C16-alkyl (EO)25-methacrylate | 21.6 1 | 0 | 0 |
| | N-dodecyl mercaptan | 0.07 | 0.3 | 0 |
| Initiator 1 | Deionised water | 4.8 | 7.1 | 46.3 |
| | Ammonium persulphate | 0.9 | 0.9 | 0.3 |
| Initiator 2 | Deionised water | 4.8 | 4.4 | 0 |
| | Sodium methabisulphite | 0.1 | 0.1 | 0 |
| Polymerisation temperature | | 80° C. | 80° C. | 85° C. |

Copolymers (CA1), (CA2) and (CA3) are obtained.

Protocol for Preparing Oil-In-Water Emulsions for Step a)

Place the ingredients for phase P1 in a beaker and place under stirring in a VMI Rayneri-type stirrer. Neutralise the mixture with the sodium hydroxide solution for phase P2 to get a pH of 7. Lastly, gradually incorporate the oil in phase P3. For an emulsion comprising Emulium Delta, phase P1 should be heated at 70-80° C. until a homogeneous mixture is obtained. In Table 2, the percentages, %, are percentages by weight relative to the total weight of the oil-in-water emulsion. The "x" value corresponds to the solids content of the anionic copolymer A or of the Emulium Delta.

TABLE 2

| Ingredients | % |
| --- | --- |
| Phase P1 | |
| Water | Qsp 100% |
| Anionic copolymer A for the examples according to the invention or Emulium Delta for the comparative example | x % |
| Phase P2 | |
| Sodium hydroxide 20% | Qsp pH 6.7-7.1 |
| Phase P3 | |
| Oil | 40 |

Shower Gel Preparation Protocol

In a beaker, under stirring using a stirrer, the Phase P' 1 ingredients are added in the order in the following table. Once the mixture is homogeneous, the ingredients in Phase P'2 are added. Lastly, the pH is adjusted using the sodium hydroxide solution in Phase P'3. The ingredients and amounts used are shown in Table 3. The percentages, %, are percentages by weight relative to the total weight of the shower gel.

TABLE 3

| Ingredients | % |
| --- | --- |
| Phase P'1 | |
| Water | Qsp 100% |
| RHEOSTYL ™ 100 30% (or Carbopol ® Ultrez 20) | 8.00% (or 0.5%) |
| Oil-in-water emulsion from step a) containing 40% oil for the examples according to the invention (or pure oil for comparative example 2) | (y/0.4) % (or y %) |
| Texapon NSO UP Sodium Laureth Sulphate 28% | 32.5% |
| Dehyton PK 45 Cocamidopropylbetaine 45% | 6.7% |
| Phase P'2 | |
| Salcare Super 7 AT1 Polyquaternium-7 40% | 0.28% |
| Phenoxyethanol | 0.5% |
| Phase P'3 | |
| Sodium hydroxide 20% | Qsp pH 6.7-7.1 |

Example 1

An oil-in-water emulsion, O/W, is prepared according to the protocol described in the introduction (Table 2). Each emulsion comprises 1% by weight of anionic copolymer A chosen among the copolymer (CA1), the copolymer (CA2) or the copolymer (CA3), defined in Table 1. Each emulsion comprises 40% by weight of sweet almond oil.

Each emulsion is then used to make a shower gel comprising 10% by weight, relative to the total weight of shower gel, of sweet almond oil according to the protocol described in the introduction (Table 3). Phase P' 1 comprises 8% by weight of Rheostyl™ 10030%.

A reference shower gel is also used, denoted as T, comprising all of the ingredients of the shower gel described in Table 3 except for the oil-in-water emulsion in step a) containing 40% oil. This reference shower gel also does not comprise oil.

For each shower gel, we measure:
the amount of foam, its stability,
the D50% and the polydispersity ((D90%−D10%)/D50%) of the oil droplets in the shower gel and
the viscosity and stability of the shower gel.
The results are shown in Table 4, n/a denotes not applicable.

TABLE 4

| | T | CA1 | CA2 | CA3 |
| --- | --- | --- | --- | --- |
| Foam (mL) | 114 | 101 | 130 | 113 |
| Foam stability (%) | 83 | 81 | 78 | 80 |
| D50% in shower gel (μm) | n/a | 3.1 | 3 | 3.1 |
| Shower gel polydispersity | n/a | 1.13 | 1.21 | 1.13 |
| Viscosity 25° C., 6 rpm (mPa · s) | 4,400 | 19,600 | 24,400 | 19,600 |
| Stability 1 month 50° C. | n/a | yes | yes | yes |

Example 2

An oil-in-water emulsion, O/W, is prepared according to the protocol described in the introduction (Table 2). Each emulsion comprises 0.7% or 1% or 1.5% by weight of anionic copolymer (CA1), defined in Table 1. Each emulsion comprises 40% by weight of sweet almond oil.

Each emulsion is then used to make a shower gel comprising 10% by weight, relative to the total weight of shower gel, of sweet almond oil according to the protocol described in the introduction (Table 3). Phase P' 1 comprises 8% by weight of Rheostyl™ 100 30.

A reference shower gel is also used, denoted as T, comprising all of the ingredients of the shower gel described in Table 3 except for the oil-in-water emulsion in step a) containing 40% oil. This reference shower gel also does not comprise oil.

For each shower gel, we measure:
the amount of foam, its stability,
the D50% and the polydispersity ((D90%−D10%)/D50%) of the oil droplets in the shower gel and
the viscosity and stability of the shower gel.
The results are shown in Table 5.

TABLE 5

| Shower Gel | According to the invention | | | Reference |
| --- | --- | --- | --- | --- |
| (CA1) content | 0.18% | 0.38% | 0.25% | 0 |
| Foam (mL) | 79 | 98 | 101 | 114 |
| Foam stability (%) | 85 | 83 | 81 | 83 |
| D50% in shower gel (μm) | 3.8 | 3 | 3.1 | n/a |
| Shower gel polydispersity | 1.08 | 1.17 | 1.13 | n/a |
| Viscosity 25° C., 6 rpm (mPa · s) | 20,200 | 26,000 | 19,600 | 4,400 |
| Stability 1 month 50° C. | yes | yes | yes | n/a |

Example 3

An oil-in-water emulsion, O/W, is prepared according to the protocol described in the introduction (Table 2). Each emulsion comprises 1% by weight of anionic copolymer (CA1), defined in Table 1. Each emulsion comprises 40% by weight of sweet almond oil. Each emulsion is then used to make a shower gel comprising 10% or 20% by weight, relative to the total weight of shower gel, of sweet almond oil according to the protocol described in the introduction (Table 3). Phase P' 1 comprises 8% by weight of Rheostyl™ 100 30%.

A reference shower gel is also used, denoted as T, comprising all of the ingredients of the shower gel described in Table 3 except for the oil-in-water emulsion in step a) containing 40% oil. This reference shower gel also does not comprise oil. For each shower gel, the content of sweet almond oil and anionic copolymer content (CA1) are shown.

For each shower gel, we measure:
the amount of foam, its stability,
the D50% and the polydispersity ((D90%−D10%)/D50%) of the oil droplets in the shower gel and
the viscosity and stability of the shower gel.
The results are shown in Table 6.

TABLE 6

| Oil content | 0 | 10.00% | 20.00% |
|---|---|---|---|
| (CA1) content | 0 | 0.25% | 0.50% |
| Foam (mL) | 114 | 101 | 83 |
| Foam stability (%) | 83 | 81 | 81 |
| D50% in shower gel (µm) | n/a | 3.1 | 3.5 |
| Shower gel polydispersity | n/a | 1.11 | 1.33 |
| Viscosity 25° C., 6 rpm (mPa · s) | 4,400 | 19,600 | 55,300 |
| Stability 1 month 50° C. | n/a | yes | yes |

Example 4

An oil-in-water emulsion, O/W, is prepared according to the protocol described in the introduction (Table 2). Each emulsion comprises 1% by weight of anionic copolymer (CA1) defined in Table 1. Each emulsion comprises 40% by weight of a vegetable oil chosen among sweet almond oil or sesame seed oil.

Each emulsion is then used to make a shower gel comprising 10% by weight, relative to the total weight of shower gel, of vegetable oil according to the protocol described in the introduction (Table 3). Phase P' 1 comprises 8% by weight of Rheostyl™ 10030%.

For each shower gel, we measure:
the amount of foam, its stability,
the D50% and the polydispersity ((D90%−D10%)/D50%) of the oil droplets in the shower gel and
the viscosity and stability of the shower gel.
The results are shown in Table 7.

TABLE 7

| Cosmetic oil B | *Prunus* oil | Sesame oil |
|---|---|---|
| Foam (mL) | 101 | 120 |
| Foam stability (%) | 81 | 78 |
| D50% in shower gel (µm) | 3.1 | 2.8 |
| Shower gel polydispersity | 1.13 | 0.92 |
| Viscosity 25° C., 6 rpm (mPa · s) | 19,600 | 22,100 |
| Stability 1 month 50° C. | yes | yes |

Example 5

An oil-in-water emulsion, O/W, is prepared according to the protocol described in the introduction (Table 2). Each emulsion comprises 1% by weight of anionic copolymer (CA1) defined in Table 1. Each emulsion comprises 40% by weight of sweet almond oil. Each emulsion is then used to make:
a shower gel GD1 comprising 10% by weight, relative to the total weight of shower gel, of sweet almond oil according to the protocol described in the introduction (table 3) for which the P'1 phase comprises 8% by weight of Rheostyl™ 100 30% or
a shower gel GD2 comprising 10% by weight, relative to the total weight of shower gel, of sweet almond oil according to the protocol described in the introduction (Table 3) for which phase P' 1 comprises 0.5% by weight of Carbopol® Ultrez 20 or
a GD3 shower gel with the composition given in Table 8.

TABLE 8

| Ingredients | % |
|---|---|
| Water | Qsp 100% |
| Oil-in-water emulsion from step a) containing 40% oil | 25% |
| Texapon NSO UP sodium laureth sulphate 28% | 32.5% |
| Dehyton PK 45 cocamidopropyl betaine 45% | 6.7% |
| Sodium hydroxide 20% | Qsp pH 6.7-7.1 |

The percentages, %, are percentages by weight relative to the total weight of the shower gel.

For each shower gel, we measure:
the amount of foam, its stability,
the D50% and the polydispersity ((D90%−D10%)/D50%) of the oil droplets in the shower gel and
the viscosity and stability of the shower gel.
The results are shown in Table 9.

TABLE 9

| | GD1 | GD2 | GD3 |
|---|---|---|---|
| Foam (mL) | 113 | 97 | 108 |
| Foam stability (%) | 80 | 80 | 84 |
| D50% in shower gel (µm) | 3.1 | 7.5 | 7.9 |
| Shower gel polydispersity | 1.13 | 1.17 | 0.96 |
| Viscosity 25° C., 6 rpm (mPa · s) | 19,600 | 1,660 | 10 |
| Stability 1 month 50° C. | yes | no* | no* |

*creaming (oil particle migration)

Comparative Example 1

Two shower gels, GD4 and GD5, each having the composition given in Table 10, are prepared.

TABLE 10

| Ingredients | GD4 % | GD5 % |
|---|---|---|
| Water | Qsp 100% | Qsp 100% |
| Sweet almond oil | 0% | 10% |
| Texapon NSO UP sodium laureth sulphate 28% | 32.5% | 32.5% |
| Dehyton PK 45 cocamidopropyl betaine 45% | 6.7% | 6.7% |
| Sodium hydroxide 20% | Qsp pH 6.7-7.1 | Qsp pH 6.7-7.1 |

The percentages, %, are percentages by weight relative to the total weight of the shower gel.

A shower gel GD6 is also prepared according to the following protocol:
An oil-in-water emulsion, O/W, is prepared according to the protocol in the introduction (Table 2), but using Emulium Delta instead of the anionic copolymer A. The emulsion comprises 6% by weight (solids content) of Emulium Delta. The emulsion comprises 40% by weight of sweet almond oil.

This emulsion is then used to make a shower gel comprising 10% by weight, relative to the total weight of shower gel, of sweet almond oil according to the protocol described in the introduction (Table 3). Phase P' 1 comprises 8% by weight of Rheostyl™ 100 30%. For each shower gel, we measure:
the amount of foam, its stability,
the D50% and the polydispersity ((D90%−D10%)/D50%) of the oil droplets in the shower gel and
the viscosity and stability of the shower gel.

The results are shown in Table 11, n.m denotes non-measurable and n/a denotes not applicable.

TABLE 11

|  | GD4 | GD5 | GD6 |
|---|---|---|---|
| Foam (mL) | 136 | n.m | 33 |
| Foam stability (%) | 81 | n.m | 91 |
| D50% in shower gel (μm) | n/a | 23.8 | 3.1 |
| Shower gel polydispersity | n/a | 1.74 | 1.21 |
| Viscosity 25° C., 6 rpm (mPa · s) | 10 | 10 | 25,000 |
| Stability 1 month 50° C. | no | no | yes |

For the shower gel GD5, the mixture formed is unstable and does not allow measures to be taken.

Comparative Example 2

In this comparative example, the sweet almond oil is introduced directly, without the preliminary step of producing an oil-in-water emulsion.

Three shower gels, GD7, GD8 and GD9 are prepared, comprising respectively 0%, 10% or 20% by weight, relative to the total weight of shower gel, of sweet almond oil according to the protocol described in the introduction (Table 3), but by introducing the oil directly, i.e. without prior emulsion. Phase P' 1 comprises 8% by weight of Rheostyl™ 100 30%.

For each shower gel, we measure:
the amount of foam, its stability,
the D50% and the polydispersity ((D90%−D10%)/D50%) of the oil droplets in the shower gel and
the viscosity and stability of the shower gel.

The results are shown in Table 12, n/a denotes not applicable.

TABLE 12

|  | GD7 | GD8 | GD9 |
|---|---|---|---|
| Oil content | 0% | 10% | 20% |
| Foam (mL) | 114 | 125 | 111 |
| Foam stability (%) | 81 | 77 | 78 |
| D50% in shower gel (μm) | n/a | 3.6 | 4.1 |
| Shower gel polydispersity | n/a | 2.12 | 1.88 |
| Viscosity 25° C., 6 rpm (mPa · s) | 4,400 | 7,660 | 8,240 |

The distribution of the oil droplets is polydisperse.

The invention claimed is:

1. A water-rinsable, aqueous cleansing formulation, comprising:
a) an anionic copolymer A comprising an ASE copolymer, a HASE copolymer, or a combination thereof;
b) a cosmetic oil component B in an amount of from 1 to 40 wt. %, relative to a total formulation weight, in the form of droplets dispersed in the aqueous phase with a polydispersity, (D90%−D10%)/D50%, of less than 1.7, wherein the droplets of the cosmetic oil component B have a D50% of from 1 μm to 50 μm; and
c) a surface-active agent C,
wherein a Brookfield viscosity of the water-rinsable, aqueous cleansing formulation measured at 6 rpms at 20° C. is at least 19,600 mPa·s,
wherein the water-rinsable, aqueous cleansing formulation is prepared by a method comprising:
(a) preparing an oil-in-water emulsion comprising, by weight, relative to a weight of the oil-in-water emulsion, from 0.5 to 4 wt. % of the anionic copolymer A comprising an ASE copolymer, a HASE copolymer, or a combination thereof; from 20 to 70 wt. % of the cosmetic oil component B; q.s.p. 100% water, by adding, under agitation at a speed of form 200 rpm to 10,000 rpm, the cosmetic oil component B to an aqueous phase (AP) having a pH at least 6.5, comprising the anionic copolymer A and water, and
(b) mixing the oil-in-water emulsion obtained in the preparing (a) with an aqueous composition comprising the surface-active agent C.

2. The formulation of claim 1, wherein the polydispersity of the droplets of the oil component B is less than 1.6.

3. The formulation of claim 1, wherein the anionic copolymer A comprises:
the ASE copolymer, which is prepared by polymerizing components comprising (a1) an anionic monomer comprising a polymerizable olefinic unsaturation; (a2) an ester of a compound derived from a carboxylic acid comprising a polymerizable olefinic unsaturation; (a4) optionally, a monomer comprising a polymerizable unsaturation and a sulfonic acid or phosphoric acid group; (a5) optionally, a hydroxy($C_1$-$C_6$)-alkyl acrylate and/or a hydroxy(C1-C6)-alkyl methacrylate; and (a6) optionally, a cross-linking monomer or a monomer comprising a first olefinic unsaturation and a second olefinic unsaturation;
the HASE copolymer, which is prepared by polymerizing components comprising: (a1) an anionic monomer comprising a polymerizable olefinic unsaturation; (a2) an ester of a compound derived from a carboxylic acid comprising a polymerizable olefinic unsaturation; (a3) an associative hydrophobic monomer: (a4) optionally, a monomer comprising a polymerizable olefinic unsaturation and a sulfonic acid or phosphoric acid group; (a5) optionally, a hydroxy(C1-C6)-alkyl acrylate and/or a hydroxy(C1-C6)-alkyl methacrylate; and (a6) optionally, a cross-linking monomer or a monomer comprising a first olefinic unsaturation and a second olefinic unsaturation,
or a combination of the ASE copolymer and HASE copolymer.

4. The formulation of claim 3, wherein:
the anionic monomer (a1) comprises acrylic acid, methacrylic acid, maleic acid, maleic anhydride, itaconic acid, crotonic acid, an acrylic acid salt, a methacrylic acid salt, a maleic acid salt, a maleic anhydride salt, an itaconic acid salt, a crotonic acid salt, or a combination thereof; or
the monomer (a2) an ester comprising, in esterified form, acrylic acid, methacrylic acid, maleic acid, maleic anhydride, itaconic acid, crotonic acid, or a combination thereof; or the monomer (a3) is a compound of the following formula (I):

$$R^1\text{-}(EO)_m\text{---}(PO)_n\text{---}R^2 \qquad (I),$$

wherein m and n are independently 0 or an integer or decimal less than 150, and m or n is different from 0, EO is independently a $CH_2CH_2O$ group, PO is independently $CH(CH_3)CH_2O$ of $CH_2CH(CH_3)O$, $R^1$ is a group comprising a polymerizable olefinic unsaturation, and $R^2$ is a straight or branched $C_6$-$C_{40}$-alkyl group, a phenyl group, or a polyphenyl group; or the monomer (a4) comprises 2-acrylamido-2-methylpropane sulfonic acid, ethoxymethacrylate sulfonic acid, sodium methallyl sulfonate, styrene sulfonate hydroxyethyl acrylate phosphate, hydroxypropyl acrylate phosphate, hydroxyethylhexyl acrylate phosphate, hydroxyethyl methacrylate phosphate, hydroxypropyl methacrylate phosphate, and/or hydroxyethylhexyl methacrylate phosphate, or a combination thereof, optionally in salt form; or the monomer (a5) comprises hydroxyethyl acrylate, hydroxypropyl acrylate, hydroxyethylhexyl acrylate, hydroxyethyl methacrylate, hydroxypropyl methacrylate, hydroxyethylhexyl methacrylate, or a combination thereof.

5. The formulation of claim 1, comprising from 5 to 35 wt. %, relative to the total formulation weight, of the cosmetic oil component B.

6. The formulation of claim 1, wherein the surface-active agent C comprises an anionic surface-active agent, an amphoteric surface-active agent, a nonionic surface-active agent, or a combination thereof.

7. The formulation of claim 1, further comprising:
a suspensivant agent.

8. The formulation of claim 1, having a pH of from 5 to 12.

9. The formulation of claim 1, which is a shower gel or a shampoo.

10. The formulation of claim 1, wherein the polydispersity of the droplets of the oil component B is less than 1.5.

11. The formulation of claim 3, wherein the anionic monomer (a1) comprises a polymerizable olefinic unsaturation and a carboxylic acid group.

12. The formulation of claim 1, wherein the D50% of the droplets of cosmetic oil component B is from 1 μm to 30 μm.

13. A method of preparing a water-rinsable, aqueous cleansing formulation, the method comprising:

(a) preparing an oil-in-water emulsion comprising, by weight, relative to a weight of the oil-in-water emulsion, from 0.5 to 4 wt. % of an anionic copolymer A comprising an ASE copolymer, a HASE copolymer, or a combination thereof; from 20 to 70 wt. % of a cosmetic oil component B; q.s.p. 100% water, by adding, under stirring, the cosmetic oil component B to an aqueous phase (AP) having a pH at least 6.5, comprising the anionic copolymer A and water, and (b) mixing the oil-in-water emulsion obtained in the preparing (a) with an aqueous composition comprising a surface-active agent C, wherein the water-rinsable, aqueous cleansing formulation, comprises:

a) an anionic copolymer A comprising an ASE copolymer, a HASE copolymer, or a combination thereof;

b) a cosmetic oil component B in an amount of from 1 to 40 wt. %, relative to a total formulation weight, in the form of droplets dispersed in the aqueous phase with a polydispersity, (D90%–D10%)/D50%, of less than 1.7, wherein the droplets of the cosmetic oil component B have a D50% of from 1 μm to 50 μm; and c) a surface-active agent C, wherein a Brookfield viscosity of the water-rinsable, aqueous cleansing formulation measured at 6 rpms at 20° C. is at least 19,600 mPa·s.

14. The method of claim 2, wherein the aqueous phase (AP) is prepared by a method comprising:

(a-i) mixing the anionic copolymer A comprising an ASE copolymer, a HASE copolymer, or a combination thereof and water; then (a-ii) adjusting the pH of the mixture obtained in the mixing (a-ii) to at least 6.5.

15. The method of claim 13, comprising, prior to the mixing (b):

(a') adjusting the pH of the oil-in-water emulsion obtained in the preparing (a) to a pH of from 5 to 12.

16. The method of claim 13, wherein the mixing (b) comprises adjusting the pH of the formulation to a pH of from 5 to 12.

17. A cleansing formulation, obtained by the method of claim 13, wherein the cosmetic oil component B is in the form of droplets dispersed in the aqueous phase and having a polydispersity, (D90%–D10%)/D50%, less than 1.7.

* * * * *